United States Patent [19]

Maier, Jr.

[11] 4,181,650

[45] Jan. 1, 1980

[54] PROCEDURE FOR THE ASSAY OF PHARMACOLOGICALLY IMMUNOLOGICALLY AND BIOCHEMICALLY ACTIVE COMPOUNDS IN BIOLOGICAL FLUIDS

[76] Inventor: Charles L. Maier, Jr., P.O. Box 232, Yardley, Pa. 19067

[21] Appl. No.: 607,151

[22] Filed: Aug. 25, 1975

[51] Int. Cl.² .................... A61K 37/26; C07C 103/52; G01N 33/16

[52] U.S. Cl. .................................. 260/112.7; 424/12; 536/7

[58] Field of Search .................... 260/112.5 R, 112.7, 260/112 R, 209 R, 236 R, 239.1, 243 C, 268 PE, 284, 285, 285.5, 250 P, 397.2; 424/12, 89, 177, 178, 179

[56] References Cited

PUBLICATIONS

Njus et al: Anal. Biochem., 61, 280–287, (1974).

*Primary Examiner*—Frederick E. Waddell
*Attorney, Agent, or Firm*—John J. Kane; Frederick A. Zoda; A. Sperry

[57] ABSTRACT

A determination of the presence and amount of a specific organic substance (ligand) that will form a complex with a macromolecule (antibody) may be made by means of a reagent obtained by binding to the ligand to be assayed a chemiluminescent substance. The addition of a limited amount of a substance (antibody) having receptors for the ligand together with the chemiluminescent labeled ligand to the fluid to be assayed results in a competitive reaction between the ligand present in the fluid and the chemiluminescent labeled ligand for the limited number of receptor sites. Under equilibrium conditions, the amount of chemiluminescent labeled ligand bound to the antibody is related to the amount of unlabeled ligand in the solution being assayed, and is determined by isolating the antibody and measuring its chemiluminescence or by isolating and measuring the amount of free labeled-ligand remaining.

7 Claims, 4 Drawing Figures

LUMINESCENT ACTIVITY OF SUCCESSIVE 1ml. FRACTIONS OF LABELED LIGAND

GEL FILTRATION (1:10 INSULIN-LUMINOL CONJUGATE)

PROCEDURE FOR THE ASSAY OF PHARMACOLOGICALLY IMMUNOLOGICALLY AND BIOCHEMICALLY ACTIVE COMPOUNDS IN BIOLOGICAL FLUIDS

BACKGROUND OF THE INVENTION

1. Field of the Invention

Methods available for the rapid accurate quantitative or qualitative determination of biologically active substances at extremely low concentrations are limited in number. The physician's diagnosis of the patient or confirmation of the diagnosis frequently involves the detection and/or quantitation of one or more substances in body fluids such as saliva, blood, or urine. The ability to rapidly detect in body fluids the presence and amounts of such materials as may be naturally synthesized by the body or ingested is often times critical to the patient's life. Such materials would include, but are not limited to, hormones of both steroid and polypeptide type, prostaglandins, toxins, and other substances which may be involved in body functions, such as thyroxine, triiodithyronine, etc. The method of assay to be useful to the physician, must be capable of differentiating between extremely small differences in concentrations or amounts of the substance.

2. Description of the Prior Art

Several methods have, in the past, been used for the assay of body fluids, notably radioassay, radioimmunoassay, thin layer chromatography and enzyme amplified assay systems.

The radioimmunoassay procedure has been described by Murphy, Journal, Clinical Endocrinology, 27, 973 (1967); Ibid, 28, 343 (1968). The use of a radioassay or radioimmunoassay technique suffers from several disadvantages among which are the hazards associated with or inherent in radioactive substances, associated handling problems, instability, the need for expensive equipment for the performance of the assays and the difficulties associated with the manipulation and separation of the free and bound forms of the radiolabled substance.

Thin layer chromatography procedures are described by Stahl, Thin Layer Chromatography, Springer Verlag, New York, 1969. The use of methods dependent upon thin layer chromatography for the analysis of trace amounts of materials requires a high degree of proficiency in the performance of the technique, a qualification which limits the usefulness of the method in general. Further, the method is often quite slow in the development of the chromatogram, is sensitive to the presence of a variety of interfering factors and suffers from fluctuations in the range of its performance characteristics or reliability.

An enzyme amplification assay is described by Rubenstein and Ullman, in U.S. Pat. No. 3,819,837. The use of this technique requires the precise and delicate manipulation of biological reagents of extremely complex nature, both with respect to their preparation, storage and usage. Thus, by virtue of their complexity and potential sensitivity to variations in environmental conditions, the enzyme amplification assays have not proven entirely satisfactory with respect to sensitivity and specificity.

It is therefore an object of the present invention to provide an improved method that will detect and accurately determine small amounts of organic substances in body fluids.

Other objects, advantages and novel features of the invention will become apparent from the following description when considered in conjunction with the accompanying drawings wherein.

SUMMARY OF THE INVENTION

Figure 1:
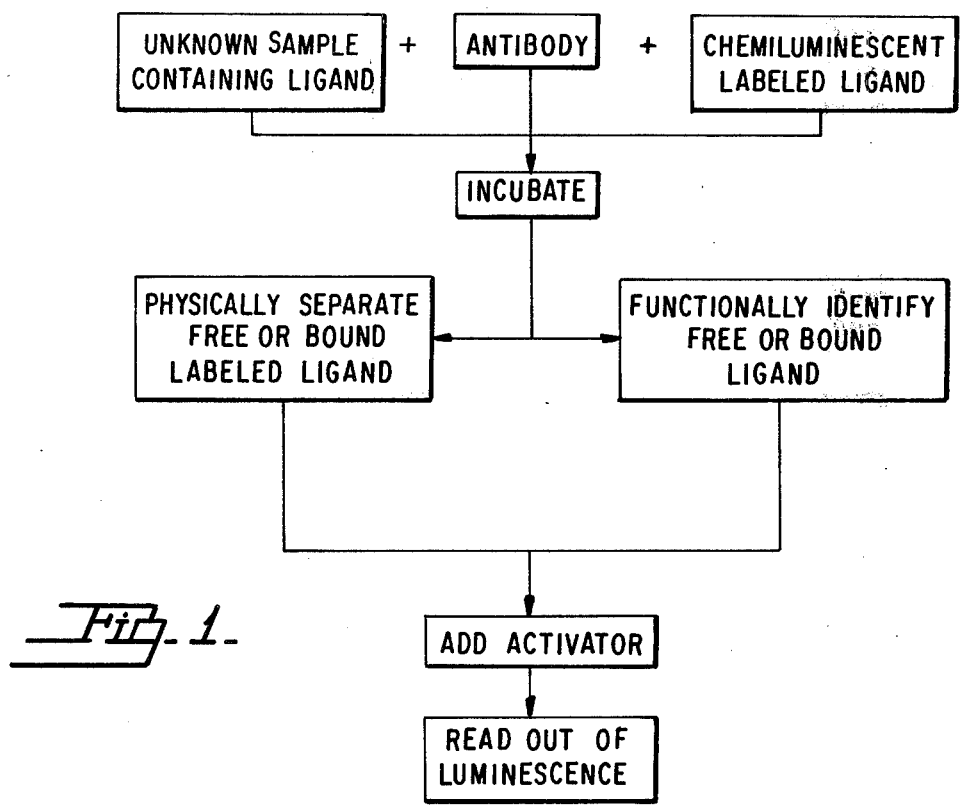
FIG. 1 is a block diagram of the assay procedure of the present invention.

The present invention provides the physician and the clinical laboratory with reagents and a method useful in detecting and assaying extremely small amounts (in the order of 5-25 ng/ml) of a wide range of organic compounds in body fluids.

The reagents of the present invention are prepared from the organic compound that is to be detected in the assay by attaching thereto a compound (such as luminol) that is capable of emitting light. Hereinafter, throughout this specification, the organic compound that is to be detected will be referred to as the ligand, (or unlabeled ligand). The reagents of the present invention are complexes formed by reacting a ligand with an organic compound having the potential of light emission and will be generally referred to throughout the specification as chemiluminescent labeled ligands; or labeled ligands.

The method of assay claimed as my invention is based on a competitive immunological reaction between an antibody to the ligand, and the ligand and chemiluminescent labeled ligand as evidenced by the following equation:

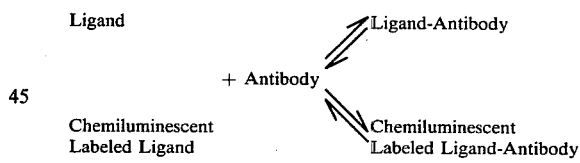

The ligand present in the patient's serum, plasma, urine or other body fluid competes with the chemiluminescent labeled ligand for the limited number of available receptor sites thereby reducing the amount of chemiluminescent ligand bound to the antibody. At equilibirum conditions, therefore, the level of chemiluminescent activity bound is inversely related to the concentration of Ligand in the patient's serum or standard. After an adequate incubation period to achieve equilibrium, the bound and free fractions are separated with either the bound or the free fraction being activated and its light emission quantitated.

DESCRIPTION OF THE SPECIFIC EMBODIMENTS

This invention provides suitable reagents and a method for detecting or assaying as little as 5-25 ng/ml of a wide range of organic materials by relating the presence of a particular unknown to chemiluminescent activity.

Various methods may be employed in assaying for a wide variety of ligands. Normally, the ligand, chemiluminescent labeled ligand and receptor will be soluble in the medium employed. The procedure is to react with a suitable antibody, simultaneously or sequentially, the ligand and labeled ligand under conditions that permit the competitive reaction between the labeled and unlabeled ligand for the receptor sites until equilibrium occurs. The physical separation of the bound ligand and labeled ligand from the unbound ligand and labeled ligand, permits one to activate the label of either the bound or unbound labeled species.

In specific instances, the method of activation may serve as the basis for the functional separation of or discrimination between the receptor bound chemiluminescent labeled ligand and that portion of the labeled ligand population which is not receptor associated or bound. In other instances accuracy may require that the bound ligand and bound labeled ligand be physically separated from the unbound ligand and unbound labeled ligand.

In measuring the chemiluminescent activity of the labeled ligand, substances, which shall be termed activators, are added to the medium. The resultant light emission is detected and recorded. In most cases, it is desirable to record the entire emission phase or total chemiluminescent activity which may range from 100–500 milliseconds to 3–5 minutes or longer. Alternatively, if the activation-emission sequence is rapid, it may be satisfactory to record the peak height of the emission. By measuring the emission characteristics of the labeled population, one may determine the amount of the labeled sustance present.

The concentration of the chemiluminescent-labeled ligands used for the assay or determination may vary widely and will depend upon a variety of factors such as the sensitivity of the detection system, and the number of chemiluminescent molecules attached to a specific ligand molecule, hereinafter referred to as the "label ratio". Furthermore, the concentration of the substance to be detected or quantitated will also influence the levels or concentration of the reactants employed for that particular test.

No upper limit may be attached to the amount of ligand that may be determined in accordance with the present invention because there are many techniques for dilution or attenuation of the signal detection system that would prevent interference if excessive levels of concentrations of labeled ligand are present. The lower limit of the concentrations of the labeled ligand which may be usefully employed for assays, is limited only by the minimum amount of chemiluminescent substance which may be detected by photodetection instruments. Since multiple chemiluminescent molecules may be attached to a single ligand molecule and photo detection instruments have been developed which will detect as little as $10^{-12}$ mole of chemiluminescent substances, the assay method of the present invention has wide application.

Within certain limits, relating to the physical and chemical characteristics of the medium, the nature of the activation and the separation process the greater the number of chemiluminescent molecules attached to a particular ligand molecule, (the label ratio) the greater the sensitivity of the assay. In such cases where multiple labels are desired, the attachment of the label may be accomplished directly by its combination with the ligand, or alternatively, several chemiluminescent molecules may first be affixed to a carrier molecule which is, in turn, linked to the ligand.

The concentration of the receptor employed for a particular test will be related generally to the range of the concentrations of the ligand to be assayed. In most cases, the solution of the ligand may be used directly, with the exception of those situations in which a relatively high concentration of ligand is present. Under such circumstances, the unknown solution may be diluted to provide a convenient concentration for assay.

Generally, the concentrations of the reagents, with the exception of the unlabeled ligand solution, are kept constant. The antibody solution to be employed may be purchased commercially or prepared by known immunological techniques. Only a small volume is required and it is maintained at the appropriate conditions of pH, ionic strength, and temperature appropriate for its activity. The assays, generally, will be conducted at moderate conditions of temperature, ranging from 10° to 50° C., at a pH in the range of 5 to 10, most often from 6 to 9. Suitable buffering substances for the method of the present invention are carbonate, borate, phosphate, (trishydroxymethyl) aminomethane and acetate.

The manner of detecting the activity of the chemiluminescent label may consist of the direct detection of the chemiluminescent reaction by measuring the visible light emitted upon activation or the activity of the chemiluminescent label may be determined by indirect methods such as fluorometry. The choice of the specific conditions to be employed for the assay will depend upon the specific requirements and conditions involved. However, normally, hydrophilic media will be utilized, particularly aqueous media. Other liquids may be present, i.e. co-solvents such as alcohols, esters, ketones, amides, etc.; the particular choice of conditions and ingredients of the medium being dependent upon the particular composition of the reagents to be employed in the assay.

With respect to the composition of the reagents to be used in the assay, it should be noted that it may be desirable to employ more than one type of labeled ligand or receptor in the performance of the assay. The use of several different antibody solutions, for example, would enable one to screen for a variety of substances simultaneously.

THE LIGANDS

Those materials of a biological, biochemical or pharmacological nature, which have been found to be suitable ligands, in the practice of my invention, are those materials for which an appropriate receptor or binding agent may be found giving satisfactory specificity and affinity for the ligand. Such ligands for which receptors may be made available range from simple molecules, such as the phenylalkylamines, notably amphetamine, and the barbiturates, to those molecules possessing a high order of complexity, e.g. proteins.

Antibodies capable of binding specifically with a ligand, may be produced by introducing that ligand (if it is antigenic) into the body or blood stream of a vertebrate. Moreover, non-antigenic ligands which are bound to other substances which are antigenic may be introduced into the circulation or body of a vertebrate, resulting in the production of antibodies to that material having receptor sites for the ligand.

Another category of ligands, based upon the nature of the receptor, is that broad class of substances or ligands for which naturally occuring receptors are available. In such instances, the receptor occurs in a living organism and may be isolated by some method or set of procedures in a form specific for the ligand. It is to be understood that the materials of biological, biochemical or pharmacological interest may have naturally occurring receptors and may also function as haptens when bonded to a receptor or carrier molecule, such as a protein.

Representative of the ligand to which a chemiluminescent material may be bound, by various methods in accordance with the present invention, are:

Class I Drugs, their metabolites or derivatives and analogs. This class includes the alkoloids, e.g. opiates, such as morphine, heroin and other compounds of similar composition, as well as the analogs of these drugs; meperidine and its analogs, catecholamines; barbiturates; glutethimide; cocaine and its metabolites and analogs; diphenylhydantoin; marijuana, tranquilizers, e.g. meprobamate, the benzdiazocycloheptanes, also known as librium, phenothiazines, etc.

Class II Amino Acids, polypepteides and proteins including: Such proteins as hemoglobin, enzymes, as well as myoglobin, which includes antibodies and immune response components. Also included are the hormones such as the adrenocorticotrophic hormone (ACTH), oxytocin, luteinizing hormone, insulin, chorionic gonadotropin, pituitary gonadotropin, growth hormone, renin bradykinin, angiotensin, follicle stimulating hormone, and thyroxine binding globulin, as well as other substances of biologically derived origin and/or effect, e.g. thyroxine, triiodithyronine, etc.

Class III Steroids, which include: The estrogens, gestrogens, androgens, adrenocortical hormones, bile acids cardiotonic glycosides, aglycones as well as saponins. As specific examples of such materials the following compounds are cited as representative: testosterone, androsterone, equilenin, estrone, estriol, progesterone, pregnenolone, 17-hydroxydeoxy-corticosterone, cortisol, aldosterone, digitoxin, digoxin, digoxigenin, digitoxigenin, etc.

Class IV Vitamins, representing a group of compounds, including: Vitamin A, the B vitamin group, the D vitamins, vitamins E and K, as well as miscellaneous substances of biological import; the antibiotics, e.g. penicillin, tetracycline, actinomycin, nucleic acids, polynucleotides, nucleosides; serotonin 3-(2 aminoethyl)-5-hydroxyindole, spermine, galactose; phenylpyruvic acid; pesticides; fungicides; namatocides; cells, living or non-living, derived from various sources, including bacterial, protosoal, plant fungal, vertebrate and non-vertebrate sources; viruses and viral particles; portions or extracts derived from cells, viruses; biological products derived as a consequence of or indicative of a specific physiologic condition or variety of conditions, such as alpha feto protein, carcinoembryonic antigen, Dane Cores, etc.

THE CHEMILUMINESCENT SUBSTANCES

The chemiluminescent substance used in the present invention is preferably luminol (5-amino-2, 3-dihydro-1, 4-phthalazinedione) in that luminol is best suited for producing quantitative and qualitative results. Other chemilunimescent materials of interest which may be used within the scope of the present invention include tetrabis (dimethylamino) ethylene, luciferin (of bacterial or firefly origin), lucigenin (dimethyl diacridinium nitrate), and oxalyl chloride. Also useful are the 2, 3-dihydrophthalazine-1, 4-diones possessing the following general structural formula:

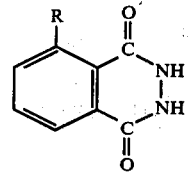

Where R may be:
NH$_2$; NCH$_3$; NHC$_2$H$_5$; NHCH$_2$C$_6$H$_5$; NHCOCH$_2$Cl;
NHCOCH$_2$NH$_2$; NHCOCH$_2$NHNH$_2$; N(CH$_3$)$_2$; N(C$_2$H$_5$)$_2$; N(CH$_2$C$_6$H$_5$)$_2$ luminol is represented by the above formula in which R=NH$_2$.

The chemiluminescent material may be attached or bonded directly to the ligand or ligand analog, or in some cases is bound to the ligand or ligand analog through a suitable coupling agent which may function as a means of attachment of the chemiluminescent substance to the ligand. A suitable coupling agent is one which does not adversely affect the ultimate chemiluminescent and biochemical properties of the labeled ligand.

The functional group which is used to conjugate the chemiluminescent substance is, in the case of lunimol, the amino group. In other compounds, such as luciferin, conjugation occurs through the hydroxy group. In general, chemiluminescent substances that have an amino group or a carboxyl group form more stable conjugates with the ligand. It is also possible to modify the functional group of a chemiluminescent substance to provide for more stable binding to the ligand without adversely affecting its chemiluminescent activity.

The linking group that may be employed for the conjugation of the chemiluminescent molecule to the ligand may vary in size from one to thirty atoms, and may include one or several of the atoms of carbon, nitrogen, phosphorous, hydrogen, sulfur and oxygen.

Examples of conjugation between a ligand (R$_1$), possessing an amino or hydroxy group and a chemiluminescent substance (R$_2$) with the same functional groups are illustrated by the following formulae:

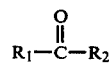

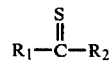

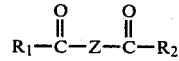

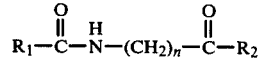

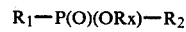

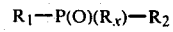

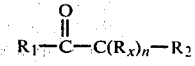

-continued

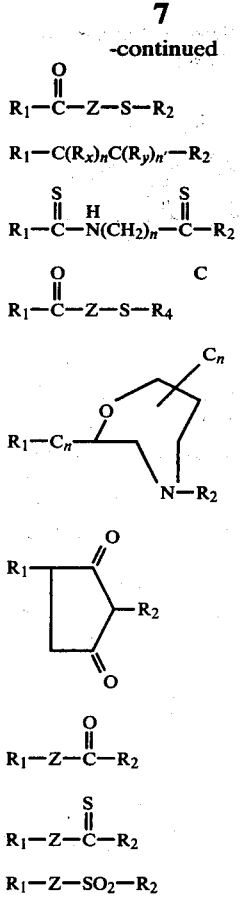

Wherein Z is a bivalent hydrocarbon group.

As one illustration of the conjugation reaction; 5-amino-2, 3-dihydro-1, 4-phthalazinedione, (luminol) may be bound through the amino group. Direct conjugation of the luminol molecule may be accomplished by a variety of methods. For example, reaction of the amino group of the luminol with thionyl chloride, with the formation of the isothiocyanate derivative, and the subsequent addition of the ligand possessing a reactive amino group, resulting in the formation of the thiourea derivative.

In the specific case where the ligand possesses a keto group, this group may be condensed with the amino group of the luminol, by treatment of the ligand with O-carboxymethyl hydroxylamine to form the carboxy methyl oxime derivative.

If a carboxyl group is present in the ligand, it may prove convenient to directly couple the ligand with the luminol molecule by the use of a reagent such as N-ethyl-3-dimethylamino-propyl carbodiimide or 1-cyclo-3-(2-morpholinoethyl)-carbodiimide. Addition of the carbodiimide reagent to the ligand, possessing the carboxyl group, results in the formation of the O-acylisourea derivative, which will react with the amino group of the luminol to effect conjugation. Alternatively, N-ethyl-5-phenyliosoxazolium-3 sulfonate (Woodward's Reagent K) may be used for the direct conjugation of the ligand with the luminol.

The presence of hydroxyl groups, as in the case of sugars or their derivatives, may permit the use of a reagent such as cyanogen bromide for the conjugation. Sugar will react with cyanogen bromide, under appropriate conditions of pH, to form the imidocarbonate, which will react with luminol, to produce either the N-substituted imidocarbonate or an N-substisuted carbamate.

An alternative procedure for the coupling of the ligand to the luminol, in those situations where the ligand possesses hydroxyl groups, as in the case of sugars, is the use of such reagents as cyanuric chloride (2,4,6-trichloro-1,3,5-triazine) or other appropriate triazine derivatives, such as 2-Amino-4,6-dichloro-s-triazine. A triazinyl derivative of the sugar is the first phase of this reaction, followed by the addition and attachment of the luminol molecule through its amino group.

Various bifunctional reagents such as glutaraldehyde may also be employed for the conjugation of a chemiluminescent substance such as luminol, to a ligand. Under the appropriate conditions of pH and concentration, addition of the luminol to the amino group of the ligand occurs with one or more than one glutaraldehyde molecule functioning as a carrier or bridge as well as a linking agent.

ACTIVATION

A variety of substances may be used, alone or together to elicit the chemiluminescent activity of the label compound(s). The following substances have been found suitable as activators for the practice of the present invention:

1. Hydrogen peroxide ($H_2O_2$);
2. Hypochlorite (OCl);
3. Sodium hydroxide (NaOH);
4. Metals, such as iron ($Fe^{+3}$), Nickel ($Ni^{+2}$), cobalt ($Co^{+2}$);
5. Iron-containing structures, such as the porphyrins and related structures (hemoglobin, cytochromes, myoglobin);
6. polyvinylpyrrolidone and other similar structures of similar activity and nature;
7. Riboflavin, and other similar materials possessing similar properties, used separately or together in reduction-oxidation reactions; and,
8. Ammonium persulfate and compounds of similar nature.

The following examples are given in order that the effectiveness of the present invention may be more fully understood. These examples are set forth for the purpose of illustration only and are not intended to in anyway limit the practice of the invention.

EXAMPLE 1—DETERMINATION OF INSULIN IN BLOOD PLASMA

A. Preparation of Insulin—Luminol Conjugate

An insulin-luminol conjugate characterized by a label ratio of 1:10 is prepared by dissolving 2.605 parts by weight of luminol in a minimum quantity of 0.01 Normal sodium hydroxide solution. The luminol solution is diluted to 1,000 parts by volume with 0.1 Molar phosphate buffer (pH 7.7).

To the solution of luminol is added with stirring an equal volume of an insulin prepared by dissolving 4.454 parts by weight bovine insulin in 1,000 parts by volume of 0.1 molar phosphate buffer (pH 7.7). Conjugation is initiated with the dropwise addition of 200 parts by volume of an aqueous 25 percent glutaraldehyde solution. The reaction flask is protected from light and the reaction is allowed to proceed for 18 hours at 25° C.

The insulin-luminol conjugate is separated from the reaction mixture by gel filtration through a 2.5 cm by 80 cm column of SEPHADEX G-10 (a polysaccharide cross-linked with ethylene chlorohydrin available from Pharmacia Fine Chemicals, of Piscataway, N.J.).

The column is equilibrated with 0.1 M phosphate buffer (pH 7.2) and the reaction mixture collected at a flow rate of 15 ml/hr.

Successive 1 ml aliquots of the effluent are checked for chemiluminescent activity in a PACKARD TRI-CARB scintillation counter. A portion (0.1 ml) of each aliquot is added to a polystyrene test tube and diluted to 2 ml with distilled water. The test tube is placed in the scintillation counter (with the coincidence circuit switched off).

An activator is prepared by mixing aqueous solutions containing 0.3% potassium ferricyanide (0.75 ml), 30% hydrogen peroxide (0.25 ml), and 10% sucrose (1 ml). This activator solution is carefully introduced by pipette into the polystyrene test tube beneath the surface of the insulin-luminol conjugate to form two layers.

Figure 2:
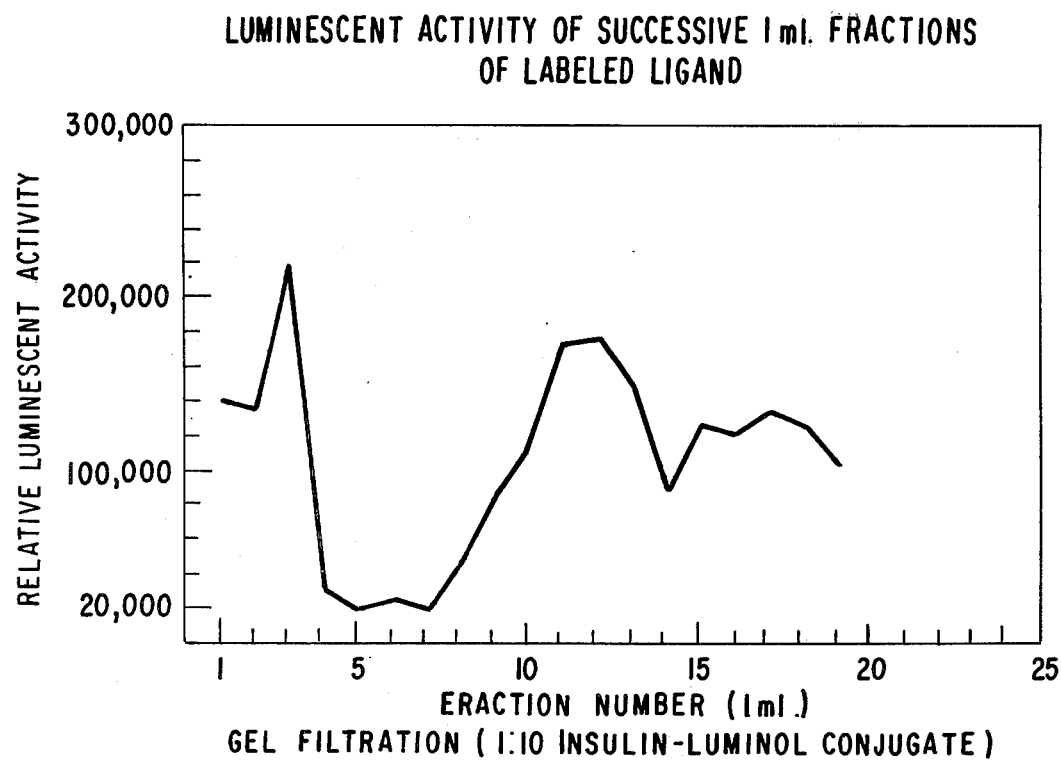
FIG. 2 is a graph showing the change in chemiluminescent activity in successive fractions of labeled ligand upon gel filtration.

Diffusion across the boundary between the insulin-luminol conjugate in the upper layer and the activator in the lower layer results in chemiluminescence which is measured by the scintillation counter. The total counts during a two minute period starting 30 seconds after introduction of the activator are recorded and plotted in FIG. 2. It will be noted from FIG. 2 that the chemiluminescent activity drops sharply with the fourth fraction. The first four aliquots are combined and this insulin-luminol conjugate solution is diluted with 9 parts by volume of 0.1 Molar phosphate buffer (pH 7.2) containing 5 mg/ml of bovine serum albumin and standardized against known amounts of Insulin to develop a curve that may be used in the rapid quantitive assay of unknown compositions.

B. Preparation of the Standard Curve (a) Eighteen numbered polystyrene tubes are washed with a 5% bovine serum albumin solution prepared in 0.04 M phosphate buffer (pH 7.4).

(b) To 16 of the numbered tubes is added 600 ul of 0.04 M phosphate buffer (pH 7.4) containing 5 mg/ml of albumin. All tubes are maintained at room temperature.

(c) One and four tenths milliliter of 0.04 M phosphate buffer (pH 7.4) is added to the tubes numbered 17 and 18.

(d) A human insulin solution is prepared by dissolving 1000 mU 5 g of human insulin in 0.1 M phosphate buffer (pH 7.7) to a final volume of 10 ml (Solution A). A dilution of the insulin solution (Solution A) is made by the addition of one volume of the insulin solution to nine volumes of 0.1 M phosphate buffer pH 7.7 to yield a final concentration of 10 mU/ml (Solution B). These standard insulin solutions are added to the numbered test tubes as follows:

| Tube No. | Insulin Standard | Insulin as uU/Tube |
|---|---|---|
| 5,6 | 50 ul Sol B | 0.5 |
| 7,8 | 100 ul Sol. B | 1.0 |
| 9,10 | 200 ul Sol. B | 2.0 |
| 11,12 | 300 ul Sol. B | 3.0 |
| 13,14 | 50 ul Sol. A | 5.0 |
| 15,16 | 100 ul Sol. A | 10.0 |

(e) To tubes 3 through 16 is added 200 ul of insulin Antiserum with gentle mixing to avoid foaming.

(f) To each of the tubes 1 through 18 is added 200 ul of the insulin-luminol conjugate prepared as described above in this example. Each tube is gently agitated to mix the contents without foaming and are capped.

(g) Tubes 1 through 18 are refrigerated at 2-4° C. for five hours.

(h) To each of tubes 1 through 18 is added with mixing 100 ul of a substitute serum prepared by dissolving 4% by weight bovine serum albumin and 3% by weight bovine gamma globulin in 0.04 m phosphate buffer (pH 7.4).

(i) To each of tubes 1 through 16 is added 0.5 ug of Dextran Coated Charcoal suspension (Schwarz/Mann), and the tubes are mixed by shaking to obtain a uniform suspension of the charcoal.

These tubes are maintained at room temperature for 10 minutes and then centrifuged at 2500 rpm for 25 minutes. The clear supernatant from each test tube is decanted into a correspondingly numbered plastic tube treated with bovine serum albumin as in step (a).

The chemiluminescent activity of each sample is determined in a Perkin-Elmer Model 124 Dual Beam Ratio Recording Spectrophotometer equipped with a strip chart recorder and a photomultiplier tube detection section.

The tube is positioned at the exit slit and the light entrance slits are blocked. Sodium hypochlorite activator (1 ml. of 0.05 Normal sodium hydroxide solution containing 0.5 percent by weight sodium hypochlorite) is introduced into the sample tube through a small bore plastic tubing in a manner that preserves the light-tight integrity of the sample compartment while permitting the introduction of the activator solution into the sample cuvette. The spectrophotometer is switched to the energy detection mode and adjusted for maximum gain. The total emission detected is recorded by a strip chart recorder and quantitated by the electronic integration of the area under the curve. The emission values (Ve) obtained from the read out are averaged in Table I.

TABLE I

| Tube No. | Average Total Count (Curve Area) | % Total Label Activity | Amount of Unlabeled Species |
|---|---|---|---|
| 1-2 | 0 | 0 | uu/ml |
| 3-4 | 10,591 | 40.8 | total label bound by ligand |
| 5-6 | 9,614 | 37.1 | 0.5 uu/ml |
| 7-8 | 7,309 | 28.2 | 1.0 |
| 9-10 | 6,220 | 24.0 | 2.0 |
| 11-12 | 5,993 | 23.1 | 3.0 |
| 13-14 | 5,708 | 22.0 | 5.0 |
| 15-16 | 5,668 | 21.8 | 10.0 |
| 17-18 | 25,945 | 100 | total label activity Insulin-Luminol conjugate |

A standardization curve is constructed by plotting the percent of the total label activity for each sample tube (containing a known quantity of insulin). This plot of the data of Table I is reproduced in FIG. 3.

Figure 3:
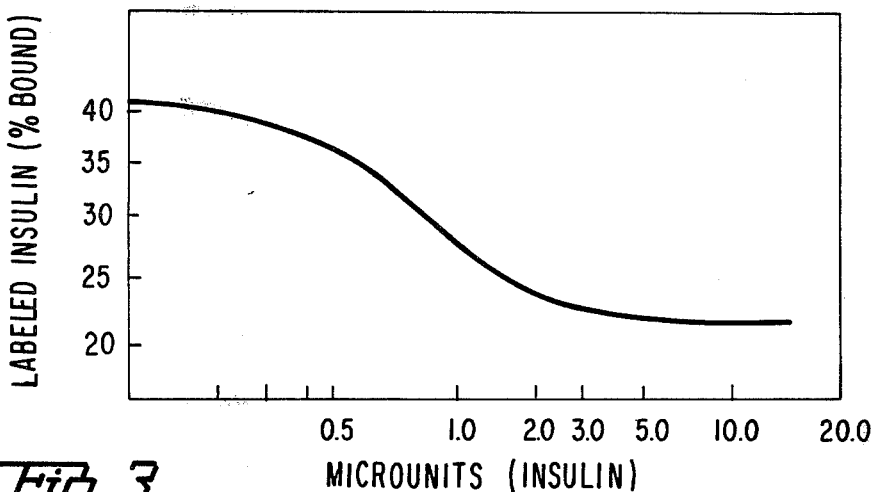
FIG. 3 is a standard curve developed in accordance with the procedure of Example I.

By using the assay procedure described above, the amount of insulin in an unknown sample may be readily determined from the intercept of the "percent bound" with the standard curve of FIG. 3.

C. Clinical Assay

Four numbered polystyrene tubes are washed with a 5% bovine serum albumin solution prepared in 0.04 m phosphate buffer (pH 7.4).

(a) Aliquots of human serum are added to these numbered polystyrene tubes as shown below:

| Tube No. | Vol. Serum |
|---|---|
| 19,20 | 100 ul |
| 21,22 | 25 ul |

Tubes 21 and 22 are recommended for a clinical assay where an insulin concentration in excess of 20 uU/ml is anticipated.

(b) To each tube is added 800 ul of 0.4 M Phosphate Buffer (pH 7.4) containing 5% of bovine albumin per liter and 100 ul of insulin-antiserum. The tubes are mixed gently to avoid foaming.

(c) To each tube is added 200 ul of the insulin-luminol conjugate prepared as described above in this example. The tubes are gently agitated to avoid foaming, each tube is capped and refrigerated at 2°–4° C. for 4.5 hours.

(d) Seventy-five microliters of substitute serum containing 4 percent bovine serum albumin and 3% bovine gamma globulin in 0.04 phosphate buffer (pH 7.4) is added to tubes 21 and 22 with thorough mixing.

(e) To each of tubes 19 through 22 is added 0.5 ml of dextran-coated charcoal suspension (Schwarz/Mann) and the tubes are mixed by shaking to obtain a uniform suspension of the charcoal. These tubes are maintained at room temperature for 10 minutes, and then centrifuged at 2500 rpm for 25 minutes. The clear supernatant from each tube is decanted into a correspondingly numbered plastic tube that has been washed with 5% bovine serum albumin in 0.04 phosphate buffer (pH 7.4).

The chemiluminescence emitted by each tube containing a decanted solution when placed in a Perkin-Elmer spectrophotometer and activated as described above, is summarized in Table II.

TABLE II

| Tube No. | Average Total Count (Curve Area) | % Total Label Activity | Amount of Unlabeled Species |
|---|---|---|---|
| 19–20 | 5,953 | 22.9 | uU/ml 3.02 |
| 21–22 | 9,370 | 36.0 | 0.73 |

The standard curve shows that 36% is equivalent to an insulin level of 0.48 uU insulin/tube. The insulin calculated as uU/ml of serum (100 ul serum sample taken) is:

uU/tube × 10 = 0.48 × 10 − 4.8 uU/ml.

EXAMPLE II—PROCEDURE FOR THE QUANTITATIVE ASSAY OF DIGOXIN LEVELS IN SERUM

A. Preparation of Digoxin-Luminol Conjugate.

A digoxin-luminol conjugate characterized by a label ratio of 1:1 is prepared by dissolving 1.00 parts by weight of Digoxin in 0.1 M acetate buffer. The digoxin solution is diluted to 500 parts by volume with additional acetate buffer and sufficient methanol is added to bring the final volume of the solution to 1000 parts. This solution is protected from light while 4.53 mg of sodium periodate is added and the mixture stirred at 25° C. for 90 minutes. At the end of this time is added 10 ml of a solution containing 0.454 mg/ml of luminol. The luminol solution is prepared by dissolving 0.453 g of luminol in the minimal amount of 0.05 N sodium hydroxide and diluting with 0.1 M acetate buffer (pH 9.5) to a final volume of 1 liter. Stirring is continued at 25° C. for an additional 120 minutes and 100 mg of sodium borohydride is added to the reaction mixture. Stirring is continued at 25° C. for another 18 hours. One milliliter of 15% ethylene glycol solution in 0.1 M acetate buffer (pH 9.5) is then added to the reaction mixture, the temperature reduced to 4° C. and stirring continued for another 48 hours.

Separation of the digoxin-luminol conjugate from the reaction mixture is achieved by selective filtration through and AMICON UM-2 filter assembly under 60 pounds nitrogen with continuous addition of fresh buffer. The pH of the added buffer is gradually decreased from 9.5 to 7.4 during the filtration procedure which is carried out over 5 days at the end of which time the filtrate exhibited no further chemiluminescence when activated with alkaline hypochlorite reagent.

The digoxin-luminol conjugate (retained by the filter) is dissolved in 100 parts by volume of 0.1 M phosphate buffer (pH 7.4) containing 5 mg/ml of bovine serum albumin and standardized against known amounts of digoxin to develop a curve that may be used in the rapid quantitative assay of unknown compositions.

B. Preparation of the Standard Curve.

The standard curve was developed by the procedure described in Example IB.

(a) To 16 numbered polystyrene tubes (washed with bovine serum albumin as described in Example IB) is added as solution of 200 ul of a standard human serum known to be free of digoxin, glycosides, or other substances that might interfere with the assay.

(b) To tube 1 and 2 is added 50 ul of 0.01 M phosphate buffer in 0.15 M saline (pH 7.4).

(c) To tubes 1 through 16 is added 1 ml of 0.01 phosphate buffer in 0.15 M saline (pH 7.4).

(d) A standard solution of digoxin in 30% ethanol (commercially available from Schwarz/Mann) is further diluted with a solution consisting of 30% ethanol in 0.01 m phosphate buffered saline (0.15 saline, pH 7.4) to produce a series of standards containing from 0.4 ng/ml to 10 ng/ml of digoxin. These standard solutions are added as follows:

| Tube | Volume | Concentration |
|---|---|---|
| 5,6 | 50 ul | 0.4 ng/ml |
| 7,8 | 50 ul | 1.0 |
| 9,10 | 50 ul | 2.0 |
| 11,12 | 50 ul | 3.0 |
| 13,14 | 50 ul | 5.0 |
| 15,16 | 50 ul | 10.0 |

(e) To tubes 3 through 16 is added 20 ul of the digoxin luminol conjugate prepared as described above in this Example.

(f) To tubes 1 through 14 is added 20 ul of digoxin antisera. The tubes are mixed well by agitation and incubated at room temperature for 30 minutes after addition to the antisera.

The chemiluminsecent activity of each sample is determined in a Perkin-Elmer Model 124 Dual Beam Ratio Recording Spectrophotometer as described in Example I above. 100 microliters of a hemoglobin solution prepared by dissolving 0.1 g of bovine hemoglobin in 1 liter of 0.1 M borate buffer (pH 10.) is added to tube 1, the tube is placed in the spectrophotometer and one minute after addition of the hemoglobin 200 ul of activator fluid, a 5% hydrogen peroxide solution in 0.1 m borate buffer (pH 10.0) is added. The total emission detected is recorded by a strip chart recorder and quantitated by the electronic integration of the area under the curve.

The procedure described in the preceding paragraph is repeated with tubes 1 through 16 and the total emission of each sample is recorded. These values (Ve) obtained from the readout are averaged in Table III.

TABLE III

| Tube No. | Average Total Integrator Count | % Total Label Activity | Amount of Unlabeled Digoxin (ng/ml) |
|---|---|---|---|
| 1,2 | 265 | 100 | Total Count |
| 3,4 | 234 | 88.3 | Total label bound by ligand |
| 5,6 | 211.7 | 79.8 | 0.08 ng/ml |
| 7,8 | 194.7 | 73.5 | 0.20 ng/ml |
| 9,10 | 164.1 | 61.9 | 0.40 ng/ml |
| 11,12 | 138.4 | 52.2 | 0.60 ng/ml |
| 13,14 | 121.6 | 45.9 | 1.0 ng/ml |
| 15,16 | 94.4 | 35.6 | 2.0 ng/ml |

A standardization curve is constructed by plotting the percent of the total label activity for each sample tube (containing a known quantity of digoxin). The plot of the data in Table III is reproduced in FIG. 4.

C. Clinical Assay.
 (1) Two numbered polystyrene tubes (17 and 18) are washed with a solution of bovine serum albumin as described above in Example IC.
 (2) Two hundred microliters of human serum to be assayed for digoxin is added to tubes 17 and 18.
 (3) To tubes 17 and 18 is added 1 ml of 0.01 M (pH 7.4) phosphate buffer in 0.15 M saline.
 (4) To tubes 17 and 18 is added 20 ul of the digoxin-luminol conjugate prepared as described above in this Example.
 (5) To tubes 17 and 18 is added 20 ul of digoxin. Both tubes are mixed well by agitation and incubated at room temperature for 30 minutes after addition of the antisera.
 (6) One hundered microliters of hemoglobin solution described above under paragraph B of this Example, is added to tubes 17 and 18. The tubes are placed in the spectophotometer and one minute after addition of the hemoglobin to each, 200 ul of the activator fluid described above in Section B of this Example, is added. The average total emission, Ve, found is 151.3 integrator units.

Figure 4:
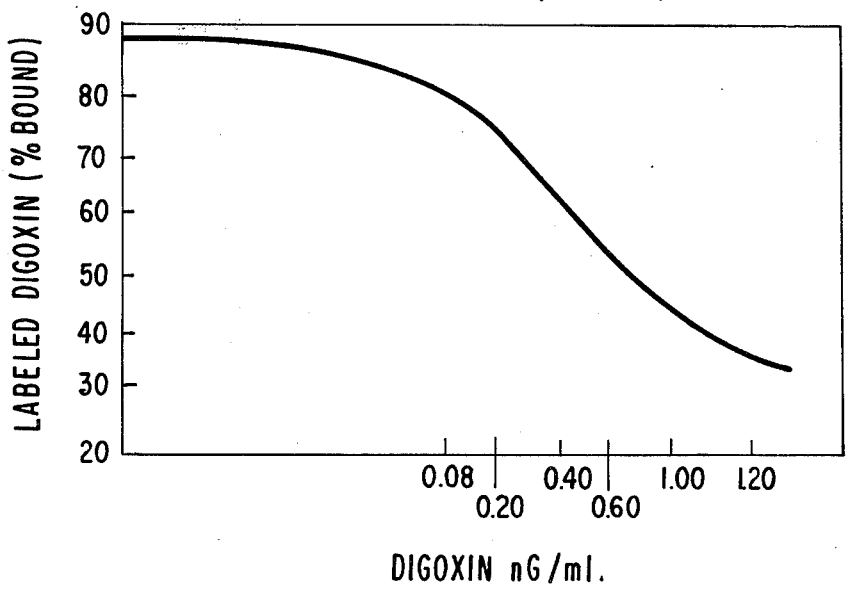
FIG. 4 is a standard curve developed in accordance with the procedure of Example II.

The intercept of the average emission value for tubes 17 and 18 on the standard curve of FIG. 4 indicate Digoxin present in the serum assayed at a level of 0.50 ng/ml.

EXAMPLE III—QUANTITATIVE ASSAY OF DIGOXIN LEVELS IN SERUM

The process described above in Example II may be modified to reduce or eliminate any inhibitory activity, if present, in human serum, plasma or other body fluid to be assayed, by adding to the serum or other body fluid in each sample tube (1 through 18) following addition of the 0.01 M phosphate buffer in 0.15 M saline, 100 ul of the globulin fraction of an anti-human serum antiserum.

It is to be understood that the foregoing disclosure is by way of specific example and that numerous modifications and variations may be practiced within the scope of the invention. The processes described in the specific Examples above can be modified to be performed by many standard, well-known techniques when desired, by special treatment of the serum, plasma or body fluids as a prerequisite to making the assay or to further use. Such specialized treatment can include, for example, mechanical filtration, dialysis or other well-known methods of molecular separation. Also numerous variations or modifications are possible with respect to the physical format of the assays, which include the use of various types of particles, added to the assay solutions or reaction systems with the intention of physically or functionally separating the antibody-associated labeled Ligand from the free (non-antibody associated) labeled Ligand. Such particle systems, for purposes of illustration, can consist of dextran coated charcoal particles or tubes, dextran particles or tubes to which an antibody has been attached, or well-known latex particle procedures.

Thus, the present invention is to be limited only to the extent set forth in the appended claims.

What is claimed is:
1. An insulin-chemiluminescent substance conjugate having luminescent activity measurable by photosensitive means.
2. The insulin-chemiluminescent conjugate of claim 1 wherein said chemiluminescent substance is selected from the group consisting of 2,3-dihydropthalizine-1,4-diones of the following general formula:

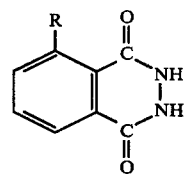

where R is:
 $NH_2$; $NCH_3$; $NHC_2H_5$; $NHCH_2C_6H_5$; $NHCOCH_2Cl$; $NHCOCH_2NH_2$; $NHCOCH_2NHNH_2$; $N(CH_3)_2$; $N(C_2H_5)_2$; $N(CH_2C_6H_5)_2$,
tetrabis (dimethylamine) ethylene, luciferin, lucigenin or oxalyl chloride.
3. The ligand-chemiluminescent conjugate of claim 1 wherein said ligand is insulin and said chemiluminescent substance is luminol.
4. An insulin-luminol conjugate prepared by reacting luminol with insulin in the presence of glutaraldehyde.
5. The insulin-luminol conjugate of claim 4 having a label ratio of about 1:10.
6. The method of activating an insulin-luminol conjugate which comprises adding thereto a solution containing an alkali metal ferricyanide and hydrogen peroxide.
7. The method of activating an insulin-luminol conjugate which comprises adding thereto an alkali metal hypochlorite.

* * * * *